(12) United States Patent
Yeh (10) Patent No.: US 9,180,331 B1
(45) Date of Patent: Nov. 10, 2015

(54) LEG REHABILITATION APPARATUS

(71) Applicant: PREVENTIVE MEDICAL HEALTH CARE CO., LTD., Taoyuan County (TW)

(72) Inventor: Ching-Yu Yeh, Taichung (TW)

(73) Assignee: PREVENTIVE MEDICAL HEALTHCARE CO., LTD., Taoyuan (TW)

( * ) Notice: Subject to any disclaimer, the term of this patent is extended or adjusted under 35 U.S.C. 154(b) by 0 days.

(21) Appl. No.: 14/497,342

(22) Filed: Sep. 26, 2014

(51) Int. Cl.
*A63B 21/00* (2006.01)
*A63B 21/02* (2006.01)
*A63B 23/035* (2006.01)

(52) U.S. Cl.
CPC ........... *A63B 21/02* (2013.01); *A63B 23/03558* (2013.01)

(58) Field of Classification Search
USPC ...................................... 482/1–148
See application file for complete search history.

(56) References Cited

U.S. PATENT DOCUMENTS

| | | | | |
|---|---|---|---|---|
| 5,492,518 A * | 2/1996 | Measom | .......... | A63B 21/00072 482/133 |
| 5,890,996 A * | 4/1999 | Frame | .................. | A63B 21/154 482/111 |
| 6,666,799 B2 * | 12/2003 | Hildebrandt | ......... | A63B 21/157 482/57 |
| 7,901,335 B2 * | 3/2011 | Webber | .............. | A63B 21/0615 482/140 |
| 8,734,304 B2 * | 5/2014 | Webber | ................ | A63B 21/062 482/140 |
| 8,870,720 B1 * | 10/2014 | Webber | ............ | A63B 21/00181 482/100 |
| 2015/0141207 A1 * | 5/2015 | Eschenbach | ......... | A63B 22/001 482/100 |

\* cited by examiner

*Primary Examiner* — Stephen Crow
(74) *Attorney, Agent, or Firm* — CKC & Partners Co., Ltd.

(57) ABSTRACT

A leg rehabilitation apparatus is provided. The leg rehabilitation apparatus includes a base, a seat, an oscillating set, a linking-up set, a resisting device and a buffer. The seat is disposed on the base. The oscillating set is pivotally connected to the base. The linking-up set is connected with the oscillating set and coupled with the oscillating set. The resisting device is connected to the oscillating set and provides a resisting force to the oscillating set during the leg rehabilitation. The buffer is disposed on the base and connected to the linking-up set. The buffer provides a buffering force during the leg rehabilitation.

18 Claims, 13 Drawing Sheets

LEG REHABILITATION APPARATUS

BACKGROUND

1. Technical Field

The present disclosure relates to a rehabilitation apparatus. More particularly, the present disclosure relates to a leg rehabilitation apparatus with buffering functionality.

2. Description of Related Art

In the conventional leg rehabilitation apparatus, a cable is commonly used for coupling with a resistance block to generate an acceptable loading for user's leg, thereby achieving physical therapy purpose. However, the conventional leg rehabilitation apparatus requires a large space to setup the resistance blocks, therefore the arrangement of the leg rehabilitation apparatus is limited by the volume of the resistance blocks.

Moreover, in the conventional leg rehabilitation apparatus, the resistance blocks are coupled with ropes to make the leg rehabilitation apparatus work reciprocally, and a large working space is required. Sometimes, a user is injured by the falling resistance blocks caused by overworking or dropping accidentally. Because the gravity of the falling resistance blocks is always over the muscle loading.

The conventional leg rehabilitation apparatus requires a lot of space to assemble, and can't prevent the user from the sport injury when accident occurring. Manufacturing a leg rehabilitation apparatus having smaller volume and can prevent from injury is one of the important issues in this field.

SUMMARY

According to one aspect of the present disclosure, a leg rehabilitation apparatus is provided. The leg rehabilitation includes a base, a seat, an oscillating set, a linking-up set and a resisting device. The seat is disposed on the base. The oscillating set is pivotally connected to the base and includes a first oscillating arm and a second oscillating arm. The first oscillating arm and the second oscillating arm are pivotally connected to the base. The linking-up set is connected with the oscillating set. The linking-up set includes a first linking component, a second linking component, a third linking component and a fourth linking component. One end of the first linking component is pivotally and coaxially connected with the first oscillating arm and the base. One end of the second linking component is pivotally and coaxially connected with the second oscillating arm and the base. The two ends of the third linking component are pivotally connected with the other end of the first linking component and the other end of the second linking component individually. One end of the fourth linking component is pivotally connected with the first linking component and the base. The resisting device is connected to the oscillating set and provides a resisting force to the oscillating set.

According to another aspect of the present disclosure, a leg rehabilitation apparatus is provided. The leg rehabilitation apparatus includes a base, a seat, an oscillating set, a linking-up set and a resisting device. The seat is disposed on the base. The oscillating set pivotally is connected to the base and includes a first oscillating arm and a second oscillating arm. The first oscillating arm and the second oscillating arm are pivotally connected to the base. The linking-up set is connected with the oscillating set. The linking-up set includes a first linking component, a second linking component, a third linking component, a fourth linking component, a linking gear and a linking chain. One end of the first linking component is pivotally and coaxially connected with the first oscillating arm and the base. One end of the second linking component is pivotally and coaxially connected with the second oscillating arm and the base. The two ends of the third linking component are pivotally connected with the other end of the first linking component and the other end of the second linking component individually. One end of the fourth linking component is pivotally connected with the first linking component and the base. The linking gear is pivotally and coaxially connected with the first oscillating arm to the base. The linking chain is engaged with the linking gear. The resisting device is connected to the oscillating set and provides a resisting force to the oscillating set.

BRIEF DESCRIPTION OF THE DRAWINGS

The present disclosure can be more fully understood by reading the following detailed description, with reference made to the accompanying drawings as follows.

DETAILED DESCRIPTION

Figure 1:
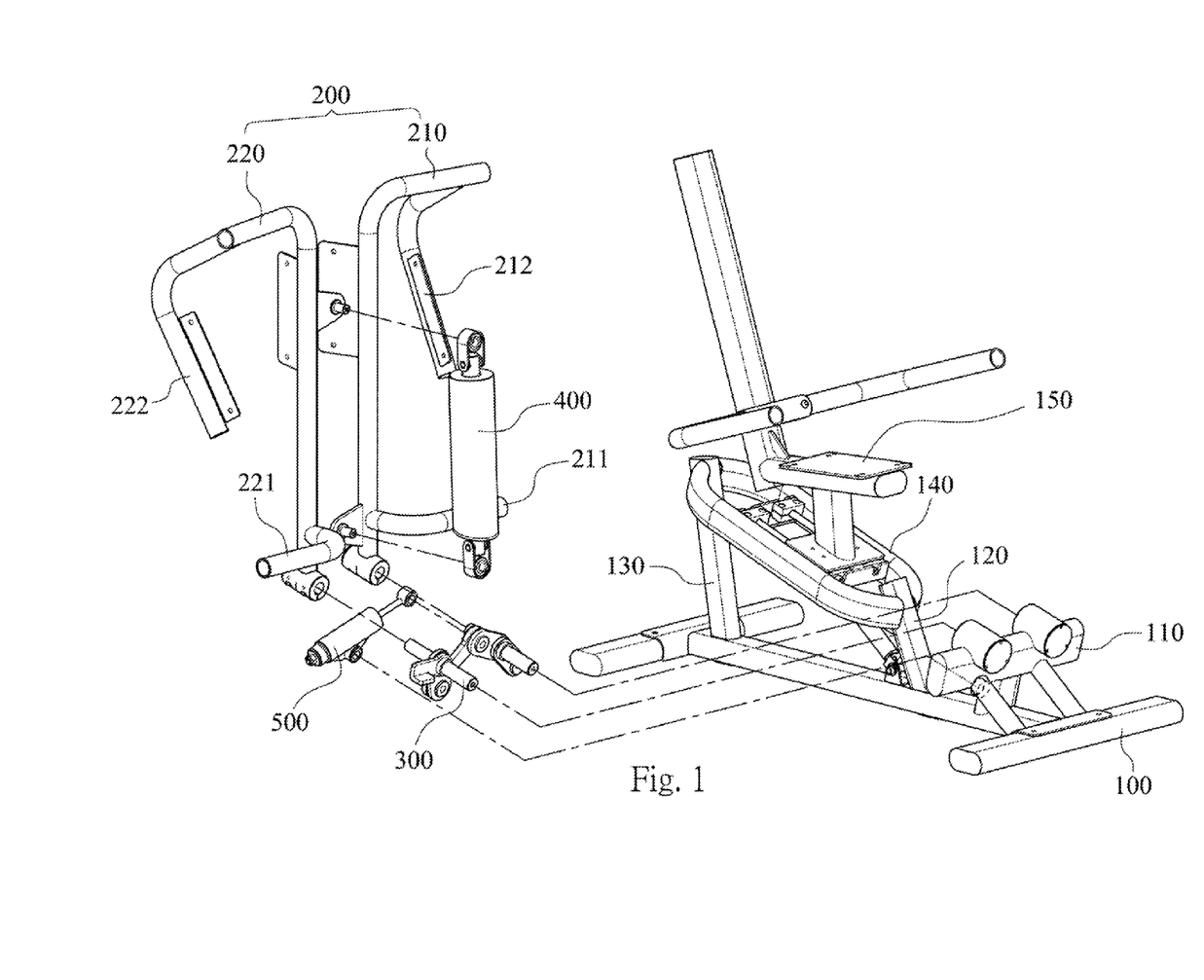
FIG. 1 is a exploded view showing a leg rehabilitation apparatus according to one embodiment of the present disclosure.
Figure 2:
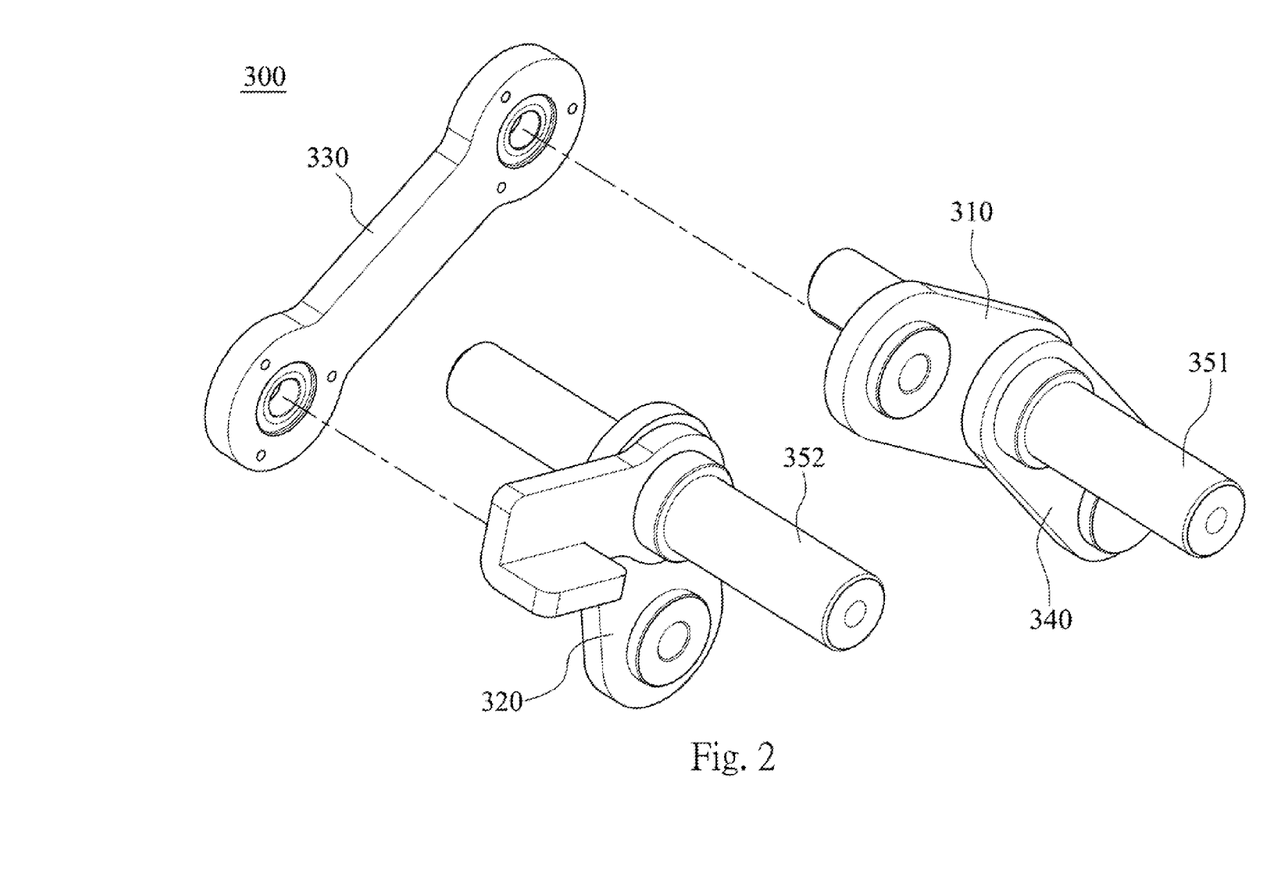
FIG. 2 is a partial exploded view of the leg rehabilitation apparatus of FIG. 1.

FIG. 1 and FIG. 2 are exploded view and partial exploded view of a leg rehabilitation apparatus according to one embodiment of the present disclosure. The leg rehabilitation apparatus includes a base 100, a seat 150, an oscillating set 200, a linking-up set 300, a resisting device 400 and a buffer 500.

The shape of the base 100 is "T" and the base 100 is used to stabilize the leg rehabilitation apparatus and allow a user to operate safely. The base 100 includes a first support component 110 which is disposed on one end of the base 100. The oscillating set 200 is pivotally disposed on the first support component 110.

The seat 150 is disposed on the base 100, and the seat 150 further includes a seat adjusting mechanism 140 which is disposed between the seat 150 and the base 100. The seat adjusting mechanism 140 is used to move the seat 150, and make sure that the user can adjust the seat 150 to the correct position. The seat adjusting mechanism 140 includes a front seat support 120 and a rear seat support 130. The front seat support 120 is disposed on a middle portion of the base 100.

The rear seat support 130 is disposed on an end of the base 100 opposite to the first supporting component 110.

The oscillating set 200 includes a first oscillating arm 210 and a second oscillating arm 220. The first oscillating arm 210 is an inverted L-shaped rod, and the bottom of first oscillating arm 210 is pivotally disposed on the first supporting component 110. The second oscillating arm 220 is also an inverted L-shaped rod, and the bottom of the second oscillating arm 220 is pivotally disposed on the supporting component 110.

The oscillating set 200 further includes two footing portions 211, 221. The two footing portions 211, 221 are used for supporting user's feet. The footing portion 211 is extended laterally from the bottom of the first oscillating arm 210, and the footing portion 221 extends laterally from the bottom of the second oscillating arm 220.

The oscillating set 200 further includes two leg supporting portions 212, 222. The leg supporting portions are used to supporting user's legs. The depending section 212 extends laterally and vertically from the top of the first oscillating arm 210. The depending section 222 extends laterally and vertically from the top of the second oscillating arm 220.

The linking-up set 300 is connected and coupled with the oscillating set 200. The linking-up set 300 includes a first linking component 310, a second linking component 320, a third linking component 330, a fourth linking component 340 and two pivot axis 351, 352. One end of the first linking component 310, one end of the fourth linking component 340 and the first oscillating arm 210 are pivotally disposed on the first supporting component 110 via the pivot axis 351. One end of the second linking component 320 and the second oscillating arm 220 are pivotally disposed on the first supporting component 110 via the pivot axis 352. Two ends of the third linking component 330 are pivotally connected with the other end of the first linking component 310 and the other end of the second linking component 320 individually.

The resisting device 400 is disposed between the first oscillating arm 210 and the second oscillating arm 220 and provides a resisting force. The resisting device 400 is a fluid pressure cylinder and two ends of the resisting device 400 are pivotally connected with the first oscillating arm 210 and the second oscillating arm 220 individually.

The buffer 500 is a spring and is disposed on the base 100. The buffer 500 is pivotally connected to the other end of the fourth linking component 340 and is coupled with the fourth linking component 340. The buffer 500 provides a buffering force during the leg exercising.

Figure 3:
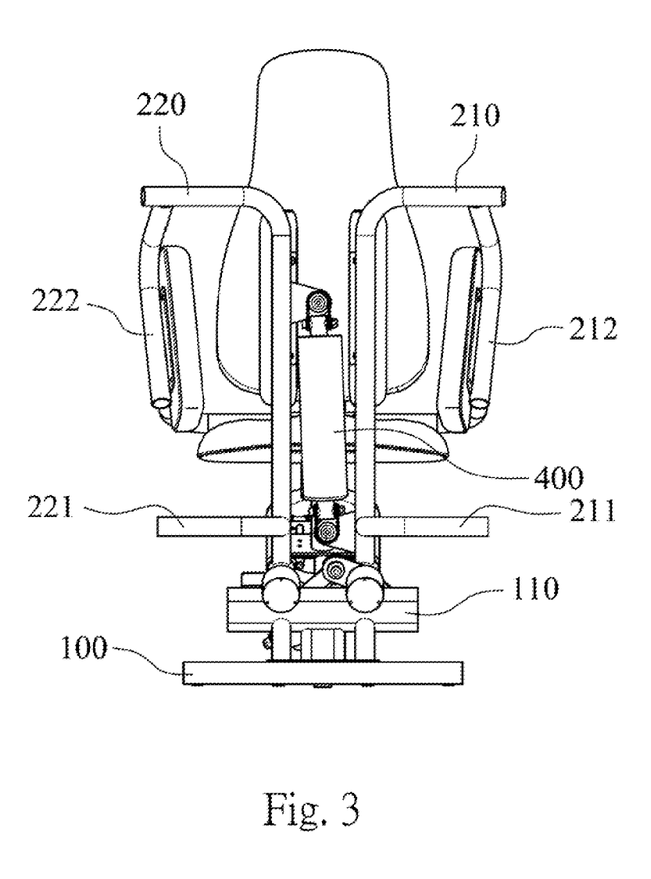
FIG. 3 is a front view showing an initial state of the leg rehabilitation apparatus of FIG. 1.
Figure 4:
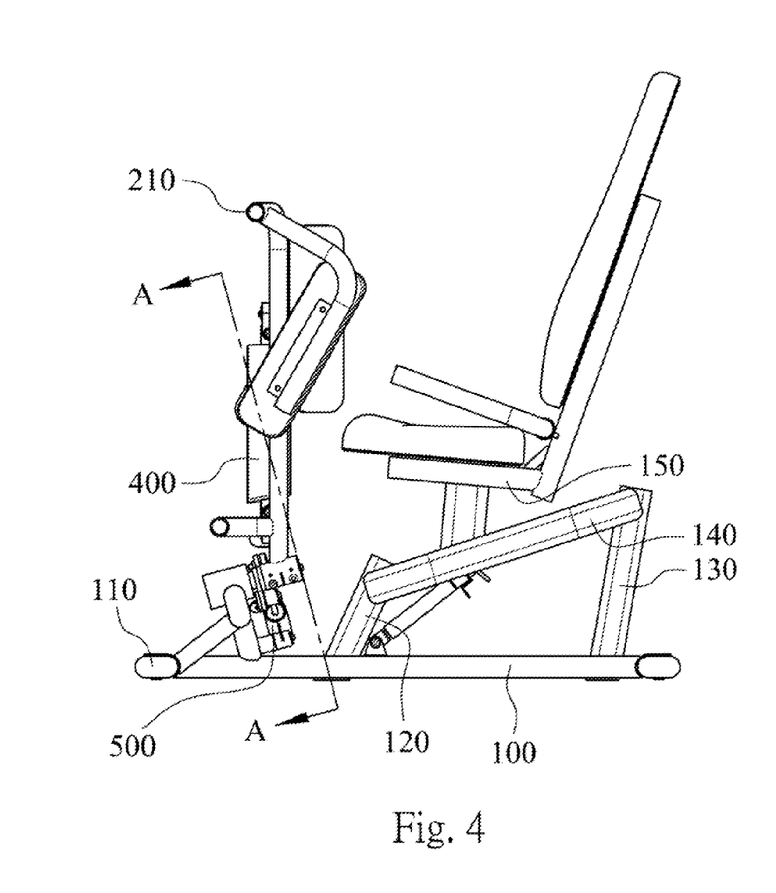
FIG. 4 is a side view showing the initial state of the leg rehabilitation apparatus of FIG. 1.
Figure 5:
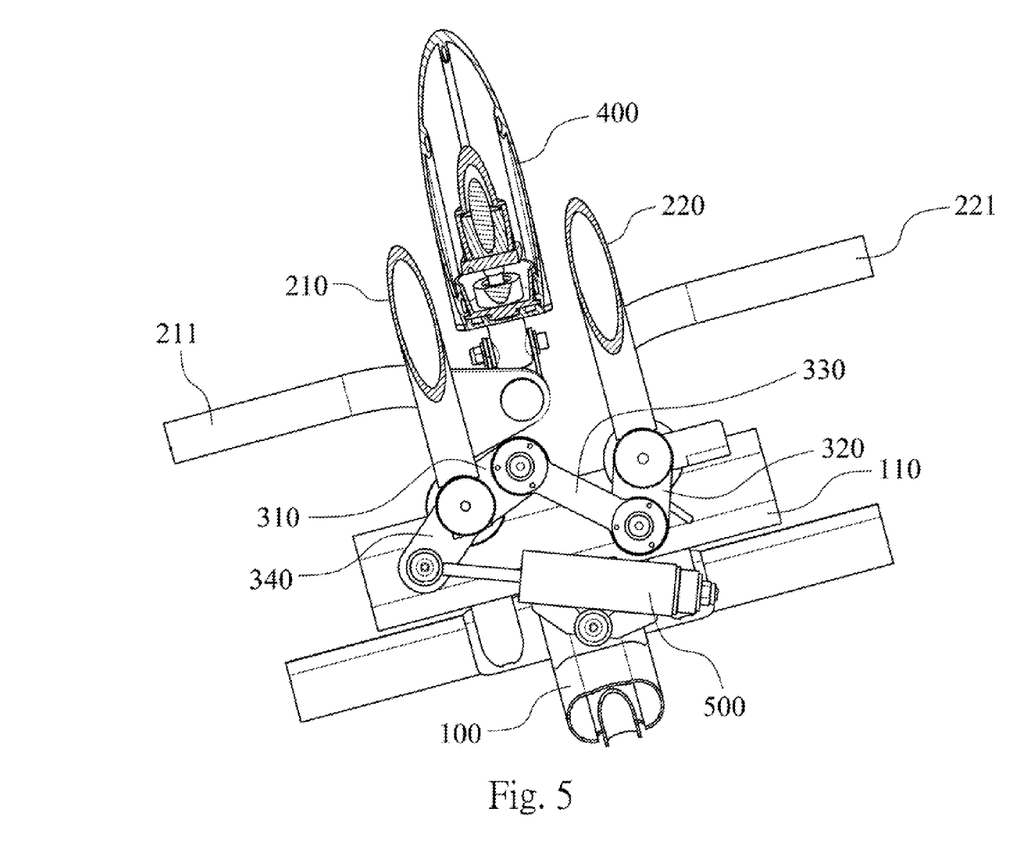
FIG. 5 is a cross-sectional view along line A-A in FIG. 4.

Taking a leg abduction as an example; an initial state of leg rehabilitation is showed in FIG. 3 to FIG. 5. At the initial state, the user seat on the seat 150 and adjust the seat 150 to a correct position by the seat adjusting mechanism 140, then the user's feet can put on the footing portions 211, 221 and then the user's leg can lean on the leg supporting portions 212, 222. In the initial state, the user doesn't force the first oscillating arm 210 and the second oscillating arm 220 to swing outward. The first linking component 310, the second linking component 320, the third linking component 330 and the fourth linking component 340 coaxially connected on the first oscillating arm 210 or the second oscillating arm 220 don't swing relatively. The resisting device 400 is vertically located between the first oscillating arm 210 and the second oscillating arm 220 and the resisting device 400 doesn't provide a resisting force. The buffer 500 isn't actuated by the fourth linking component 340 and doesn't provide a buffering force.

Figure 6:
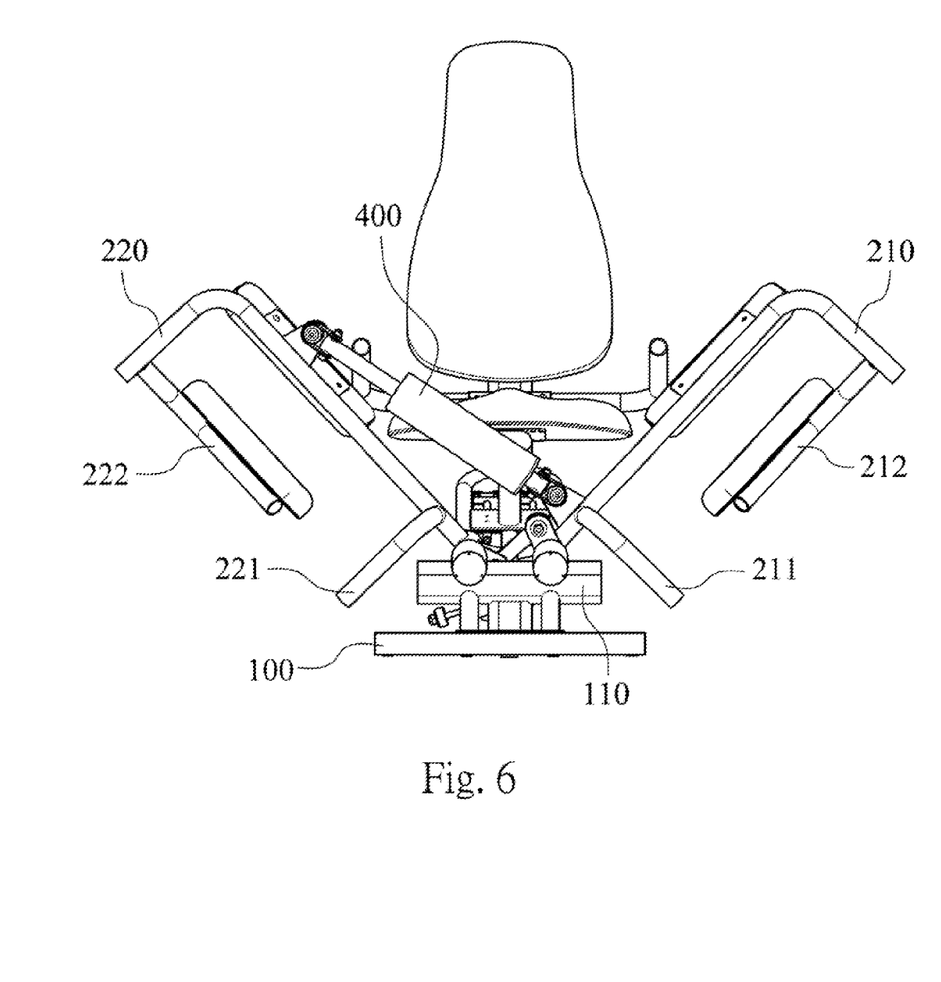
FIG. 6 is a front view showing an operating state of the leg rehabilitation apparatus of FIG. 1.
Figure 7:
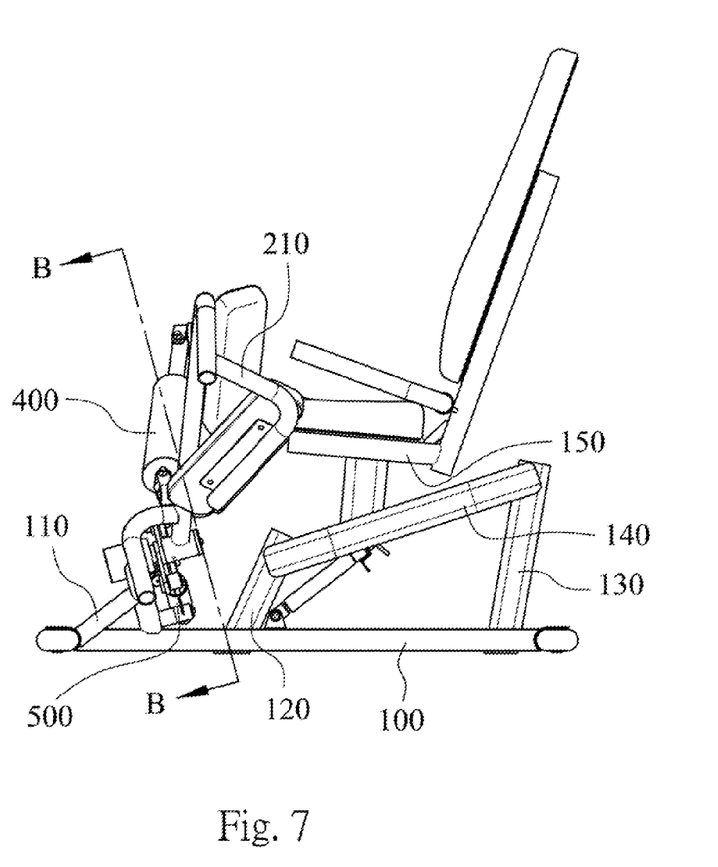
FIG. 7 is a side view showing the operating state of the leg rehabilitation apparatus of FIG. 1.
Figure 8:
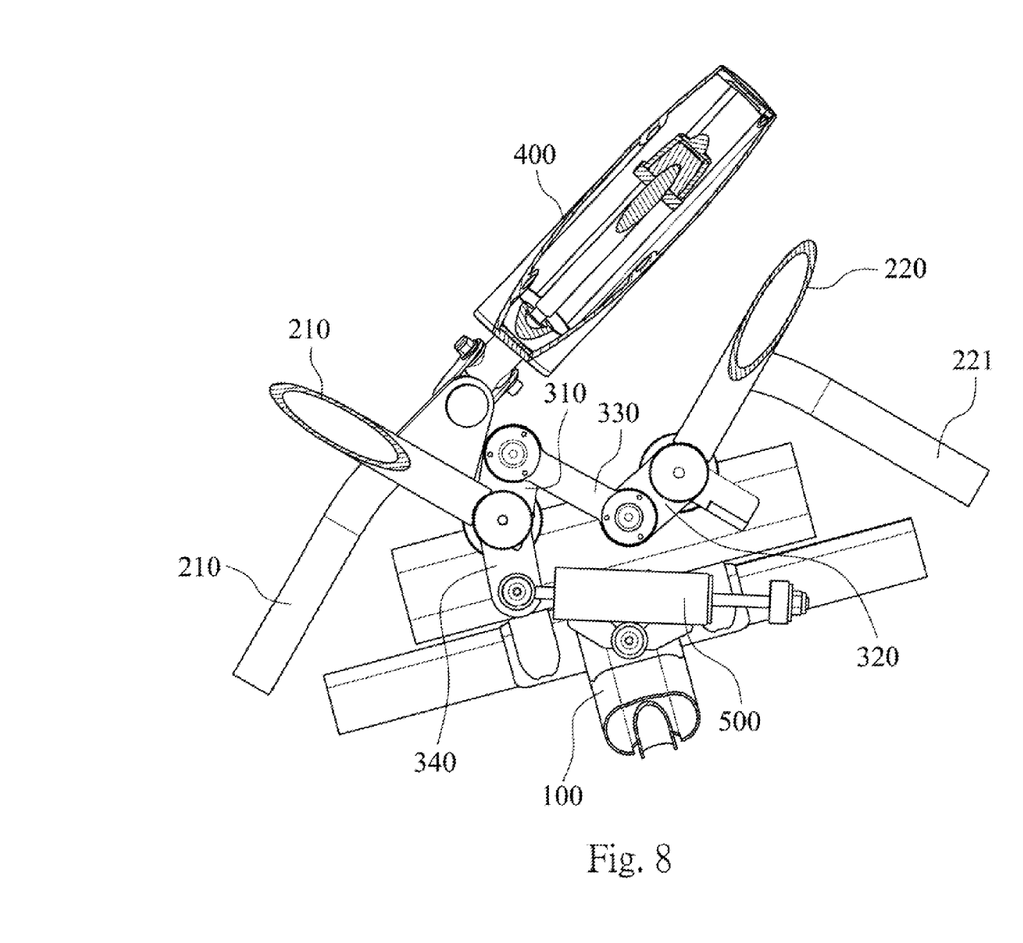
FIG. 8 is a cross-sectional view along line A-A in FIG. 4.

An operating state of leg rehabilitation is showed in FIG. 6 to FIG. 8. When the user's legs are abducted, the user forces the first oscillating arm 210 and the second oscillating arm 220 to swing outward. The first oscillating arm 210, the first linking component 310 and the fourth linking component 340 swing in the counterclockwise direction. The second oscillating arm 220 and the second linking component swing in the clockwise direction. The third linking component 330 is pivoted the first oscillating arm 210 and the second oscillating arm 220, therefore the third linking component 330 can keep in the first oscillating arm 210 and the second oscillating arm 220 to swing outward synchronously. The resisting device 400 is stretched by the first oscillating arm 210 and the second oscillating arm 220 and generates a resisting force. The resisting force is an extra loading during the leg abduction, and the leg's muscle can be trained by the extra loading. After finishing the leg abduction, the first oscillating arm 210 and the second oscillating arm 220 swing in an opposite direction which is caused by the resisting device 400. The first oscillating arm 210, the first linking component 310 and the fourth linking component 340 swing in the clockwise direction synchronously via the pivot axis 351. The second oscillating arm 220 and the second linking component 320 swing in the counterclockwise direction synchronously via the pivot axis 352. The buffer 500 pivotally connected to the fourth linking component 340 provides a buffering force to reduce the force caused by the opposite swing of the first oscillating arm 210 and the second oscillating arm 220. The resisting force of the present disclosure is not produced by gravity; therefore the resisting force 400 can reduce the leg loading at the leg adduction and can prevent from a secondary sport injury.

Figure 9:
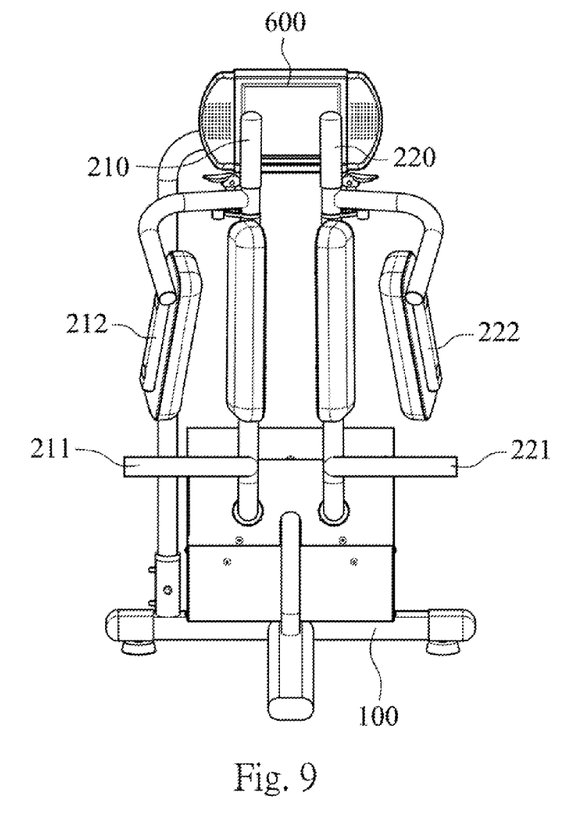
FIG. 9 is a partial front view showing a leg rehabilitation apparatus according to another embodiment of the present disclosure.
Figure 10:
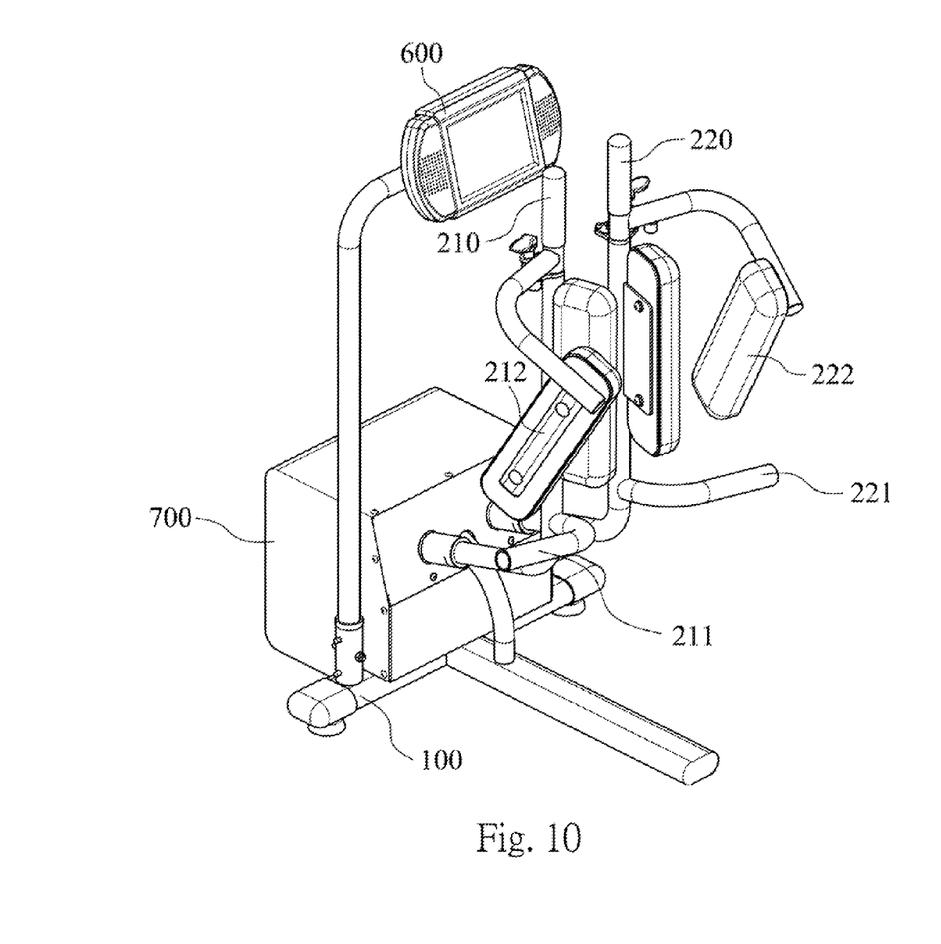
FIG. 10 is a partial perspective view of the leg rehabilitation apparatus of FIG. 9.
Figure 11:
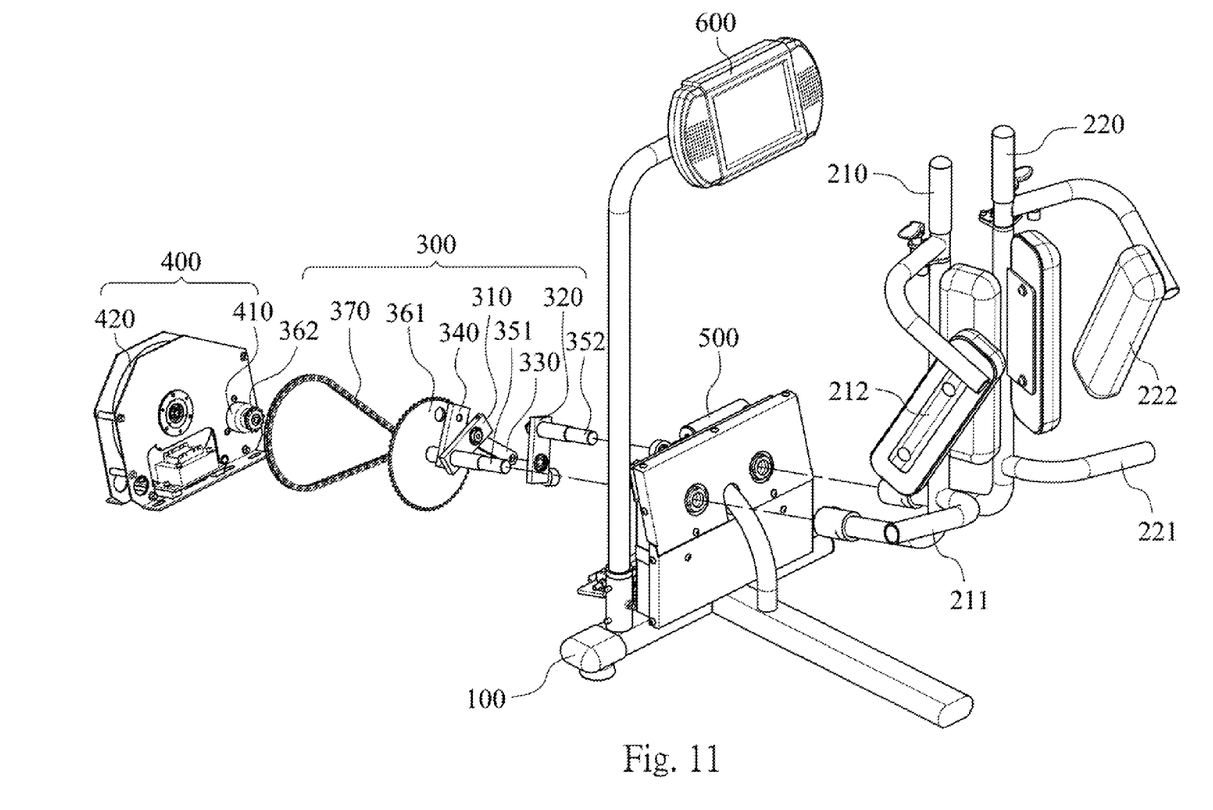
FIG. 11 is a exploded view of the leg rehabilitation apparatus of FIG. 9.

FIG. 9 to FIG. 11 show a leg rehabilitation apparatus according to another embodiment of the present disclosure. The leg rehabilitation includes a base 100, a seat, an oscillating set 200, a linking-up set 300, a resisting device 400, a buffer 500, a display device 600 and a case 700. The detail configuration between the base 100 and the seat is the same as the pervious embodiment. The case 700 is used to contain and protect the linking-up set 300, the resisting device 400 and the buffer 500.

The oscillating set 200 is the major motion mechanism of the leg rehabilitation apparatus. The oscillating set 200 includes a first oscillating arm 210 and a second oscillating arm 220. The first oscillating arm 210 is an inverted L-shaped rod, and the bottom of the first oscillating arm 210 is pivotally connected to the first supporting component 110. The second oscillating arm 220 is also an inverted L-shaped rod, and the bottom of the second oscillating arm 220 is pivotally connected to the supporting component 110.

The oscillating set 200 further includes two footing portions 211, 221, and a user's feet can be place on the footing portions 211, 221 comfortably. The footing portion 211 is disposed on the bottom of the first oscillating arm 210 and the footing portion 211 extends to the left side. The footing portion 221 is disposed on the bottom of the second oscillating arm 220 and the footing portion 221 extends to the right side.

The oscillating set 200 further includes two leg supporting portions 212, 222. The leg supporting portions 212, 222 are used to support with the user's legs. The depending section 212 extends laterally and vertically from the top of the first oscillating arm 210. The depending section 222 extends laterally and vertically from the top of the second oscillating arm 220.

Figure 12:
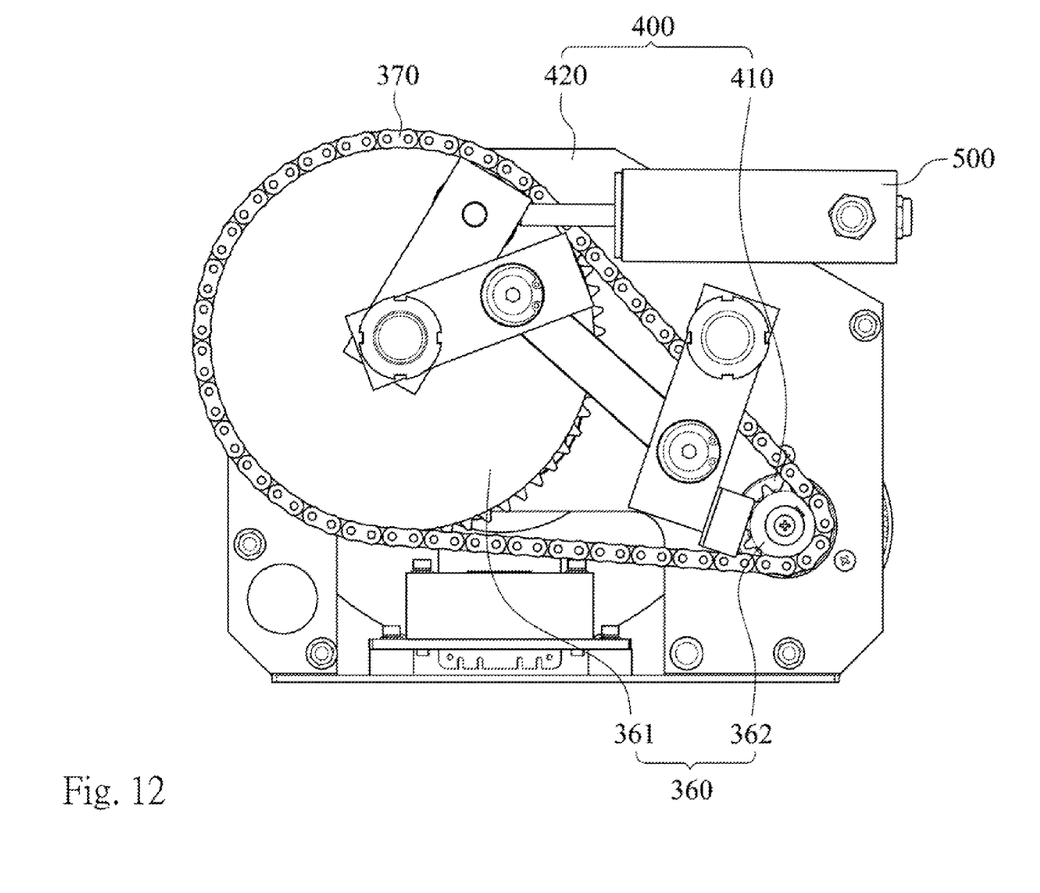
FIG. 12 is a partial view showing a linking-up set, a resisting device, and a buffer of FIG. 9.
Figure 13:
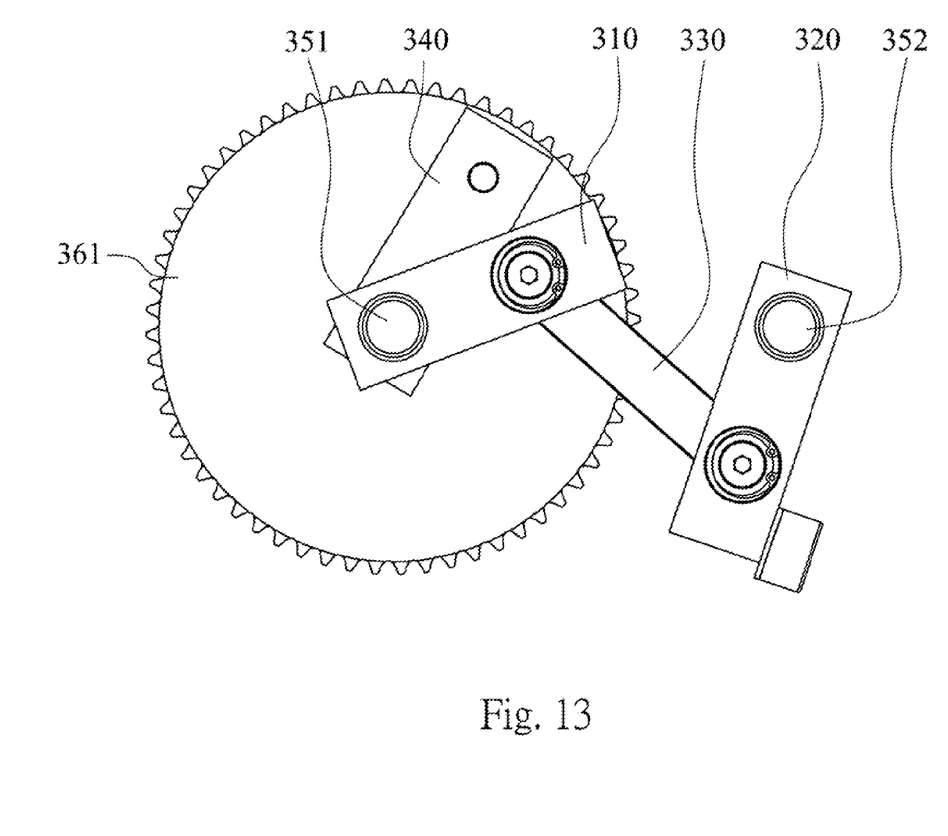
FIG. 13 is a schematic view showing the linking-up set of FIG. 9.

A configuration of the linking-up set 300, the resisting device 400 and the buffer 500 are showed in FIG. 12 and FIG. 13. The linking-up set 300 is actuated with the oscillating set 200. The linking-up set 300 includes a first linking component 310, a second linking component 320, a third linking component 330, a fourth linking component 340, a linking gear 360 and a linking chain 370. The linking-up set 300 further includes two pivot axes 351, 352. The first linking component 310, the fourth linking component 340 and the first oscillating arm 210 are pivotally connected on the first supporting component 110 via the pivot axis 351. The second linking component 320 and the second oscillating arm 220 are pivotally connected on the first supporting component 110 via the pivot axis 352. Two ends of the third linking component 330 are pivoted on the first linking component 310 and the second linking component 320 individually. The linking gear 360 includes a first linking gear 361 and a second linking gear 362. The first linking gear 361 is pivoted on the base 100 with the first linking component 310 and the fourth linking component 340 by the pivot axis 351. The second linking gear 362 is pivoted on the resisting device 400. The linking chain 370 is engaged with the first linking gear 361 and the second linking gear 362, and is synchronized with the first linking gear 361 and the second linking gear 362.

The resisting device 400 provides an adjustable resisting force by an electromagnetic effect and is coupled with the linking-up set 300. The resisting device 400 includes an evaluating device 410 and an electromagnetic device 420. The resisting device 400 is connected to the linking-up set 300 and coupled with the oscillating set 200. The electromagnetic device 420 is connected and coupled with the first linking gear 361. In FIG. 13, the first linking gear 361 is pivotally connected with the first linking component 310 and the fourth linking component 340, and the first linking gear 361 is coupled with the first oscillating arm 210. In FIG. 12, the linking chain 370 is engaged with the first linking gear 361 and the second linking gear 362, wherein the first linking gear 361 actuates the second linking gear 362, and the second linking gear 362 actuates the evaluating device 410. The evaluating device 410 evaluates a leg rehabilitation status by calculating the cycles and the rotation speed of the second linking gear 362. The electromagnetic device 420 includes an induction coil and a magnet, wherein the induction coil has a relative motion to the magnet and provides an induction current. The induction current provides an induction magnetic force which opposite the relative motion. The induction magnetic force is used as the resisting force. Furthermore, the electromagnetic device 420 can control the resisting force by adjusting the induction current.

The buffer 500 is disposed on the base 100 and is pivotally connected to another end of the fourth linking component 340. The buffer 500 is coupled with the fourth linking component 340 and generates a buffering force.

The display device 600 facing the user is disposed on the base 100 and is connected with the evaluating device 410. The display device 600 shows the leg rehabilitation status. Furthermore, the display device 600 can connect with a computer or an operation unit to record a rehabilitation progress.

As mentioned in the embodiments of the present disclosure, the user forces the first oscillating arm 210 and the second oscillating arm 220 to swing outward at leg abduction. The first oscillating arm 210, the first linking component 310 and the fourth linking component 340 swing in the counterclockwise direction synchronously at the pivot axis 351. The second oscillating arm 220 and the second linking component 320 swing in the clockwise direction synchronously at the pivot axis 352. The third linking component 330 is pivoted the first oscillating arm 210 and the second oscillating arm 220, therefore the third linking component 330 can maintain the first oscillating arm 210 and the second oscillating arm 220 swing outward synchronously. The electromagnetic device 420 is actuated by the first linking gear 361 and provides an induction magnetic force in the clockwise direction. After finishing the leg abduction, the first oscillating arm 210 and the second oscillating arm 220 swing inwards and the linking-up set 300 is actuated oppositely. The buffer 500 is compressed by the fourth linking component 340 and provides an elastic force. The buffer 500 uses the elastic force as a buffering force to reduce the resisting force and the loading of the leg for preventing from a secondary sport injury. During the leg adduction, the resisting force and the buffering force which opposite to the leg abduction is provided. The evaluating device 410 connected to the second linking gear 362 is actuated by the oscillating set 200 through the linking chain 370. Therefore, the evaluating device 410 can evaluate the user's rehabilitation status. The display device 600 shows the user's rehabilitation status to remind the user; therefore the user can modify the rehabilitation progress. Moreover, the loading of the leg rehabilitation can be adjusted immediately by adjusting the electromagnetic force and prevent the user from being injured by overloading.

In summary, the leg rehabilitation of the present disclosure has following advantages: 1. Preventing a user from injury during the rehabilitation process. 2. The volume and space of the leg rehabilitation apparatus can be reduced without using resistance blocks. 3. Adjusting the resisting force immediately to prevent the user from rehabilitating under excessive loading. 4. Showing an instant rehabilitation status and reminding the user to rearrange the rehabilitation progress and schedule.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A leg rehabilitation apparatus, comprising: a base; a seat disposed on the base; an oscillating set pivotally connected to the base, the oscillating set comprising: a first oscillating arm pivotally connected to the base; and a second oscillating arm pivotally connected to the base; a linking-up set connected with the oscillating set, the linking-up set comprising: a first linking component, wherein one end of the: first linking component is pivotally and coaxially connected with the first oscillating arm and the base; a second linking component, wherein one end of the second linking component is pivotally and coaxially connected with the second oscillating arm and the base; a third linking component, wherein two ends of the third linking component: are pivotally connected with the other end of the first linking component and the other end of the second linking component individually; and a fourth linking component, wherein one end of the fourth linking component: is pivotally connected with the: first linking component and the base; and a resisting device connected to the oscillating set and providing a resisting force to the oscillating set; wherein the oscillating set further comprises two footing portions disposed on the first oscillating arm and the second oscillating arm individually for supporting the user's feet.

2. The leg rehabilitation apparatus of claim 1, wherein the base further comprises a first supporting component, and the first oscillating arm and the second oscillating arm are pivotally connected to the first supporting component.

3. The leg rehabilitation apparatus of claim 1, further comprising:
   at least one seat adjusting mechanism, wherein the seat adjusting mechanism is disposed on the base and connected to the seat to adjust a position of the seat.

4. The leg rehabilitation apparatus of claim 1, wherein the oscillating set further comprises two leg supporting portions, the leg supporting portions are disposed on a side of the first oscillating arm and a side of the second oscillating arm individually for supporting user's legs.

5. The leg rehabilitation apparatus of claim 1, wherein the resisting device is a pressure cylinder, one end of the resisting device is connected to the first oscillating arm, the other end of the resisting device is connected to the second oscillating arm, and the resisting device is stretched or compressed by the first oscillating arm and the second oscillating arm, thereby generating the resisting force.

6. The leg rehabilitation apparatus of claim 1, wherein the pressure cylinder is a gas pressure cylinder or a fluid pressure cylinder.

7. The leg rehabilitation apparatus of claim 1, wherein the resisting force is an elastic force, a magnetic force or an electromagnetic force.

8. The leg rehabilitation apparatus of claim 1, further comprising:
   a buffer disposed on the base, the buffer being connected to the oscillating set and providing a buffering force to the oscillating set.

9. The leg rehabilitation apparatus of claim 8, wherein the buffer comprises a spring, one end of the spring is connected to the base and the other end of the spring is connected to the fourth linking component.

10. The leg rehabilitation apparatus of claim 8, wherein the buffering force is a magnetic force or an electromagnetic force.

11. A leg rehabilitation apparatus, comprising: a base; a seat disposed on the base; an oscillating set pivotally connected to the base, comprising: a first oscillating arm pivotally connected to the base; and a second oscillating arm pivotally connected to the base; a linking-up set connected with=the oscillating set, comprising: a first linking component, wherein one end of the first linking component is pivotally and coaxially connected with the first oscillating arm and the base; a second linking component, wherein one end of the second linking component is pivotally and coaxially connected with the second oscillating arm and the base; a third linking component, wherein two ends of the third linking component are pivotally connected with the other end of the first linking component and the other end of the second linking component individually; a fourth linking component, wherein one end of the fourth linking component is pivotally connected with the first linking component and the base; a linking gear pivotally and coaxially connected to the base; and a linking chain engaged with the linking gear; and a resisting device connected to the oscillating set and providing a resisting force to the oscillating set; wherein the oscillating set further comprises two footing portions, the two footing portions are disposed on a side of the first oscillating arm and a side of the second oscillating arm individually for supporting the user's feet.

12. The leg rehabilitation apparatus of claim 11, wherein the base further comprises a first supporting component, and the first oscillating arm and the second oscillating arm are connected to the first supporting component.

13. The leg rehabilitation apparatus of claim 11, further comprising:
   at least a seat adjusting mechanism, wherein the seat adjusting mechanism is disposed on the base and connected to the seat to adjust a position of the seat.

14. The leg rehabilitation apparatus of claim 11, wherein the oscillating set further comprises two leg supporting portions, the leg supporting portions are disposed on a side of the first oscillating arm and a side of the second oscillating arm individually for supporting user's legs.

15. The leg rehabilitation apparatus of claim 11, wherein the resisting device is connected to the linking gear and is actuated with the linking-up set.

16. The leg rehabilitation apparatus of claim 11, wherein the resisting force is an elastic force, a magnetic force or an electromagnetic force.

17. The leg rehabilitation apparatus of claim 11, further comprising:
   a buffer disposed on the base, one end of the buffer being connected to the other end of the fourth linking component and providing a buffering force to the oscillating set.

18. The leg rehabilitation apparatus of claim 17, wherein the buffering force is an elastic force, a magnetic force or an electromagnetic force.

* * * * *